(12) United States Patent
Fu

(10) Patent No.: US 8,486,181 B2
(45) Date of Patent: Jul. 16, 2013

(54) SLOW RELEASING DEVICE FOR GASEOUS CHLORINE DIOXIDE AND METHOD FOR MAKING SAME

(76) Inventor: Hsin-Chiao Fu, Kaohsiung (TW)

( * ) Notice: Subject to any disclaimer, the term of this patent is extended or adjusted under 35 U.S.C. 154(b) by 263 days.

(21) Appl. No.: 12/947,990

(22) Filed: Nov. 17, 2010

(65) Prior Publication Data
US 2012/0118429 A1    May 17, 2012

(51) Int. Cl.
*C01B 11/02* (2006.01)
*B01D 53/02* (2006.01)

(52) U.S. Cl.
USPC ............................................ 95/132; 423/477

(58) Field of Classification Search
USPC .............. 95/132, 900, 902, 903; 96/108, 148; 206/0.7; 423/477; 252/176, 186.1; 222/3
See application file for complete search history.

(56) References Cited

U.S. PATENT DOCUMENTS

| | | | | |
|---|---|---|---|---|
| 3,911,080 A | * | 10/1975 | Mehl et al. | 423/210 |
| 5,126,070 A | * | 6/1992 | Leifheit et al. | 252/186.36 |
| 5,360,609 A | * | 11/1994 | Wellinghoff | 514/772.3 |
| 5,573,743 A | * | 11/1996 | Klatte et al. | 423/477 |
| 5,650,446 A | * | 7/1997 | Wellinghoff et al. | 514/772.3 |
| 6,503,419 B2 | * | 1/2003 | Klatte | 252/187.23 |
| 2005/0235830 A1 | * | 10/2005 | Hughes | 96/108 |
| 2009/0297629 A1 | * | 12/2009 | Harrison et al. | 424/661 |

FOREIGN PATENT DOCUMENTS

| EP | 2110411 A1 | * | 10/2009 |
|---|---|---|---|
| WO | WO 2006/119428 A2 | * | 11/2006 |

* cited by examiner

*Primary Examiner* — Frank Lawrence, Jr.
(74) *Attorney, Agent, or Firm* — Rosenberg, Klein & Lee

(57) ABSTRACT

A method for making a slow releasing device for slowing releasing chlorine dioxide includes sending gaseous chlorine dioxide into a receiving container containing a plurality of particulate carriers. Each particulate carrier has a plurality of pores in a surface thereof. The receiving container is placed in a low-temperature environment below 30° C. The gaseous chlorine dioxide is absorbed by the particulate carriers. The particulate carries is packaged in at least one container that is subsequently sealed. The gaseous chloride dioxide can be purified before entering the receiving container. Superfluous chloride dioxide can be dissolved or absorbed in water in an absorbing tank on a circulating pipeline connected to the receiving container via an outlet pipe.

7 Claims, 5 Drawing Sheets

```
┌─────────────────────────┐
│   preparing gaseous     │
│   chlorine dioxide      │
└─────────────────────────┘
             ⇓
┌─────────────────────────┐
│   purifying gaseous     │
│   chlorine dioxide      │
└─────────────────────────┘
             ⇓
┌─────────────────────────────────────┐
│ sending gaseous chlorine            │
│ dioxide into a low-temperature      │
│ environment containing particulate  │
│ carriers; gaseous chlorine dioxide  │
│ absorbed by the particulate carriers│
└─────────────────────────────────────┘
             ⇓
┌─────────────────────────────┐
│ packaging the particulate   │
│ carriers into a container   │
└─────────────────────────────┘
             ⇓
┌─────────────────────────┐
│  sealing the container  │
└─────────────────────────┘
```

FIG. 1

SLOW RELEASING DEVICE FOR GASEOUS CHLORINE DIOXIDE AND METHOD FOR MAKING SAME

BACKGROUND OF THE INVENTION

The present invention relates to a slow releasing device for slowly releasing gaseous chlorine dioxide and a method for making the slow releasing device and, more particularly, to a method and a product of carrying gaseous chlorine dioxide in carriers to provide slow, long-term, effective release of chloride dioxide.

Chlorine dioxide is a strong oxidant having excellent effect in disinfection and sterilization and has been known as highly-effective disinfectants, sterilizers, and water-cleaning agents around the globe. The World Health Organization has classified chlorine dioxide as an A1 class (highly safe) disinfectant.

Since gaseous chlorine dioxide is unstable and apt to decompose, the storage, transportation, and use are limited during preparation of liquid chlorine dioxide. Conventionally, there are two main methods of producing solid chlorine dioxide (or dubbed as "stable chlorine dioxide"). One of the methods includes processing gaseous chlorine dioxide into stable solution of chlorite ion (such as by mixing chlorite ion into an alkaline buffer solution). Next, a solidifying agent and a stabilizer are used to absorb the stable solution of chlorite ion and then mixed with a solid acid. The resultant mixture is packaged. In the other method, sodium chlorite and sodium chlorate are used as the matrix, gel is used as auxiliary material, and an acidic substance is used as an activator. These materials are mixed and packaged.

In the above-mentioned methods, the products are solid type and in the form of powders, granules, or ingots, providing slowly-releasing solid products for slowly absorbing moisture. In addition, the solid products can be thrown into water to obtain water solution of gaseous chlorine dioxide after dissolution of the chemical agents. Examples of the methods have been disclosed in Taiwan Patent Application Nos. 087107160, 096102799, 096105956, and 096116154 and U.S. Pat. No. 4,689,169.

However, the by-products and residual organic and inorganic substances in the above-mentioned methods cause reaction of the gaseous chlorine dioxide and oxidizable substances in the water to form ions of chlorite, chlorate, and chloride salts. The desired gaseous chlorine dioxide could not be obtained.

In addition to the stable chlorine dioxide products, water solutions of chlorine dioxide are available on the market, examples of which have been disclosed in U.S. Pat. Nos. 5,296,108 and 5,993,864. However, these products still have many disadvantages. Firstly, conventional manufacturers dissolve chlorine dioxide in water. Thus, the chlorine dioxide is transported or stored in the form of water solution no matter electrolysis or chemical methods are used. However, the gaseous chlorine dioxide is instable and decays in the water into ions of chlorite, chlorate, and chloride salts. Secondly, in a case that the electrolysis equipment is in the same location of user to allow on-site preparation of water solution of chlorine dioxide, a professional worker is required to operate the electrolysis equipment, which is inconvenient to ordinary users. Thirdly, in a case that the chemical methods are used on the site in which various chemical agents are mixed and thrown into the water to produce water solution of chlorine dioxide after chemical reaction in the water, care attention is required to avoid strong reaction must be avoid, and residual chemical substances and by-products are inevitable.

BRIEF SUMMARY OF THE INVENTION

In view of the foregoing disadvantages in the prior art, the present invention provides, in a first aspect, a method for making a slow releasing device for slowing releasing chlorine dioxide including sending gaseous chlorine dioxide into a receiving container containing a plurality of particulate carriers. Each of the plurality of particulate carriers has a plurality of pores in a surface thereof. The receiving container is placed in a low-temperature environment below 30° C. The gaseous chlorine dioxide is absorbed by the plurality of particulate carriers. The plurality of particulate carries is packaged in at least one container that is subsequently sealed.

According to a second aspect of the present invention, a slow releasing device for slowing releasing gaseous chlorine dioxide includes a sealed container receiving a plurality of particulate carries. Each of the plurality of particulate carriers has a plurality of pores in a surface thereof. Gaseous chlorine dioxide is absorbed in the plurality of particulate carriers in the sealed container.

The present invention will become clearer in light of the following detailed description of illustrative embodiments of this invention described in connection with the drawings.

DESCRIPTION OF THE DRAWINGS

FIG. 1 shows a flowchart of a method for making a slow releasing device for slowly releasing gaseous chlorine dioxide according to the present invention.

DETAILED DESCRIPTION OF THE INVENTION

Figures 2, 2A:
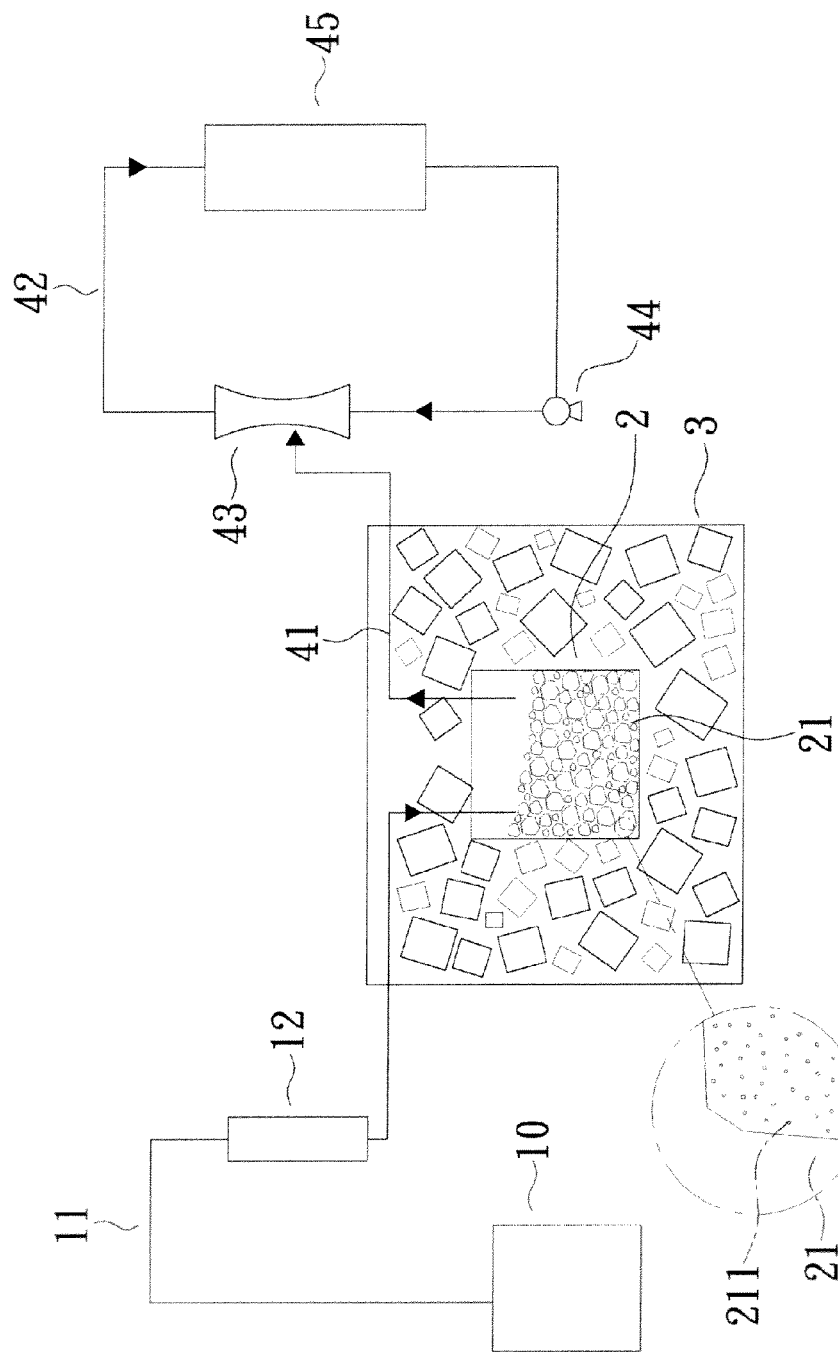
FIG. 2 shows a schematic view of an example of carrying out the method for making the slow releasing device according to the present invention.
FIG. 2A shows an enlarged view of a circled portion of FIG. 2.

With reference to FIGS. 1 and 2, an example of a method for making a slow releasing device for slowing releasing chlorine dioxide according to the present invention generally includes, but not limited to, the following steps:

1. Preparing gaseous chlorine dioxide by electrolysis or chemical methods.

2. Purifying the gaseous chlorine dioxide.

3. Entering the gaseous chlorine dioxide into a receiving container 2 receiving a plurality of particulate carriers 21. The receiving container 2 can be made of glass, plastic, or stainless steel. The receiving container 2 can be in the form of a conic bottle or other forms such as a pyramid, sphere, or cube. Each particulate carrier has a plurality of pores 211 in a surface thereof. The receiving container 2 is placed in a low-temperature environment below 30° C. In fact, under the lower temperature makes the better absorbing efficiency. The gaseous chlorine dioxide is absorbed by the particulate carriers 21.

Figure 5B:
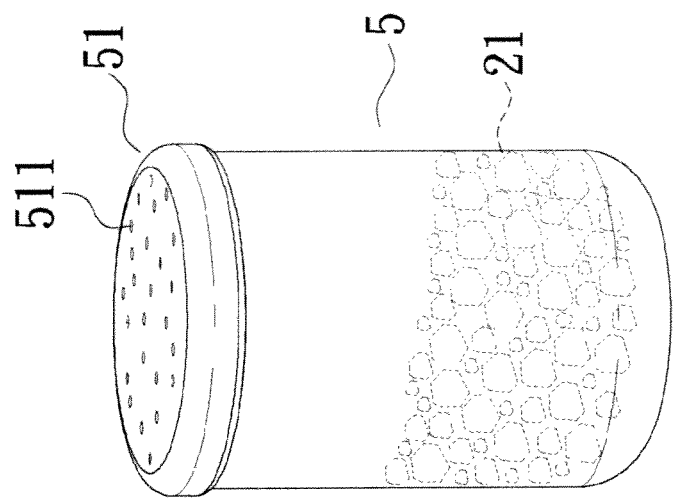
FIG. 5B shows the slow releasing device of FIG. 5A with a top cover punched to form a plurality of holes.

4. Packaging the particulate carries 21 in at least one container 5 (FIG. 5).

5. Sealing the container 5.

The container 5 includes a top cover 51 that can be punched to form a plurality of holes 511 (FIG. 5B) when in use. Thus, gaseous chlorine dioxide absorbed in the carriers 21 can be slowly and effectively released for a long period of time.

Thus, when in use, the container 5 can be unsealed by punching or opening the top cover 51. Gaseous chlorine dioxide is, thus, released to the atmosphere through release of the pressure in the container 5. Alternatively, the carriers 21 can be directly thrown into water of a predetermined amount to obtain a water solution of chlorine dioxide of a specific concentration. Chlorine dioxide based disinfectant is, thus, easily obtained. Regardless of use of gaseous chlorine dioxide or its water solution, no on-site equipment for preparing the gaseous chlorine dioxide is required. Furthermore, the container 5 is easy to store, carry, and transport while simplifying the using methods.

With reference to FIG. 2, in the step of sending gaseous chlorine dioxide into the receiving container 2, gaseous chlorine dioxide is sent from a gaseous chlorine dioxide of chemical or electrolysis generating source 10 through an inlet pipe 11 and passes through a purifying unit 12 to purify the gaseous chlorine dioxide before entering the receiving container 2. An outlet pipe 41 is connected to the receiving container 2. Superfluous gaseous chlorine dioxide not absorbed by the particulate carriers 21 exits the receiving container 2 via the outlet pipe 41. A circulating pipeline 42 is provided and includes a venturi 43 connected to the outlet pipe 41. A circulating pump 44 is mounted on the circulating pipeline 42. The circulating pump 44 creates a suction force at the venturi 43 to suck superfluous gaseous chlorine dioxide out of the receiving container 2. An absorbing tank 45 is mounted on the circulating pipeline 42. The absorbing tank 45 can receive water for dissolving or absorbing the superfluous gaseous chlorine dioxide. The absorption effect of gaseous chlorine dioxide by the carriers 21 is stable. The amount of gaseous chlorine dioxide absorbed by the carriers 21 can be controlled through control of the contact time between gaseous chlorine dioxide and the carriers 21.

Preferably, each particulate carrier 21 is selected from a group consisting of celite, kaolinite, bentonite, zeolite, porphyries andesite, powders of bamboo charcoal, calcium oxide, calcium silicate, silica gel, porous ceramic balls, activated aluminum oxide, a molecular sieve, and combinations thereof. Preferably, the molecular sieve is one of crystalline alumino silicate and a carbon molecular sieve.

Due to the small pores 211 providing a large absorbing area larger than the surface area, the carriers 21 selected from the above group provide excellent effect of absorbing gaseous chlorine dioxide. Thus, the carriers 21 are excellent solid carriers for gaseous chlorine dioxide.

The low-temperature environment can be created by placing the receiving container 2 in a trough 3 receiving a cooling medium. The trough 3 can be made of glass, plastic, stainless steel, or Dewar Caddie. In view of consideration of easy supply and costs, the cooling medium is preferably selected from a group consisting of low-temperature water, ice, dry ice, and liquefied nitrogen. However, other cooling media can be used.

Figure 3:
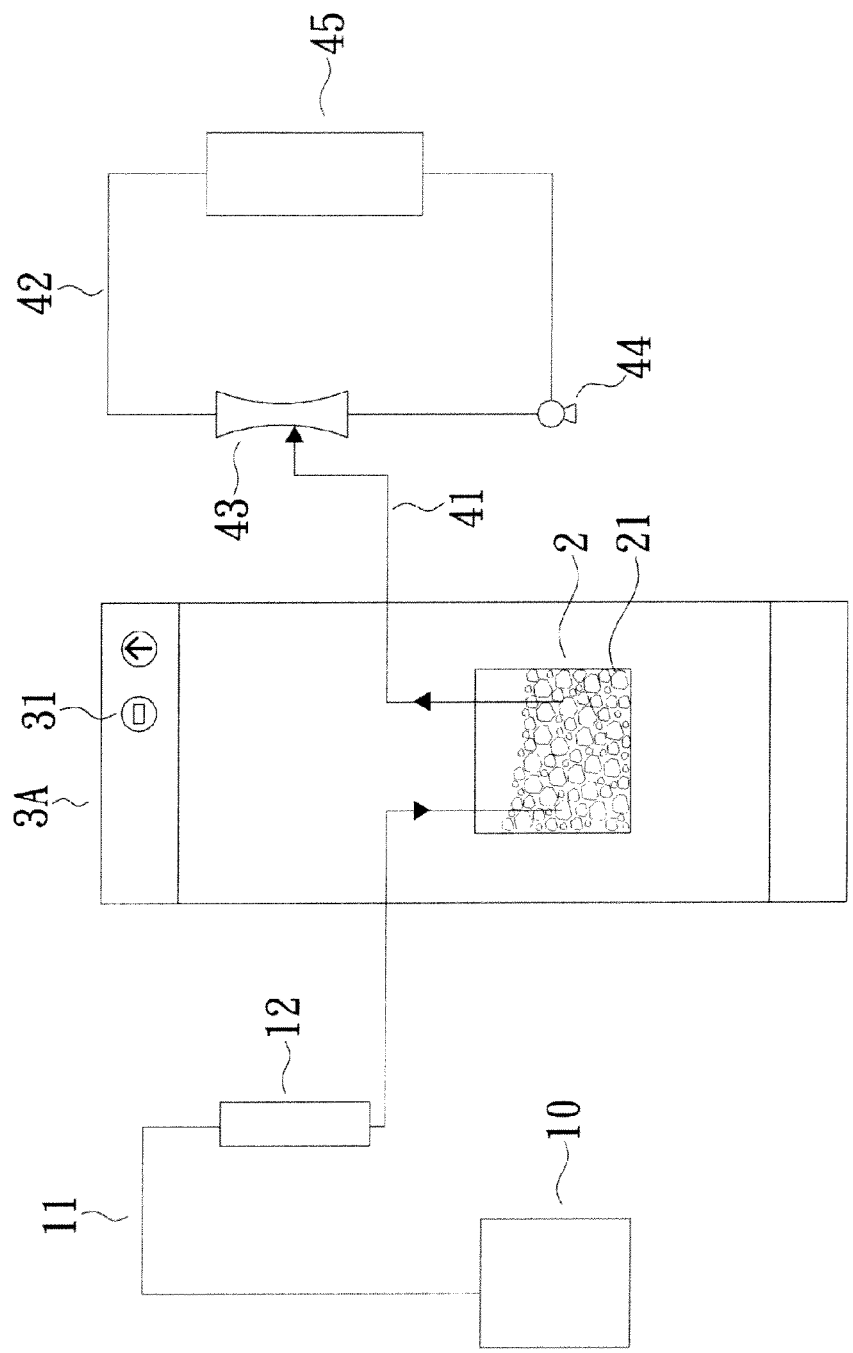
FIG. 3 shows a schematic view of another example of carrying out the method for making the slow releasing device according to the present invention.
Figure 4:
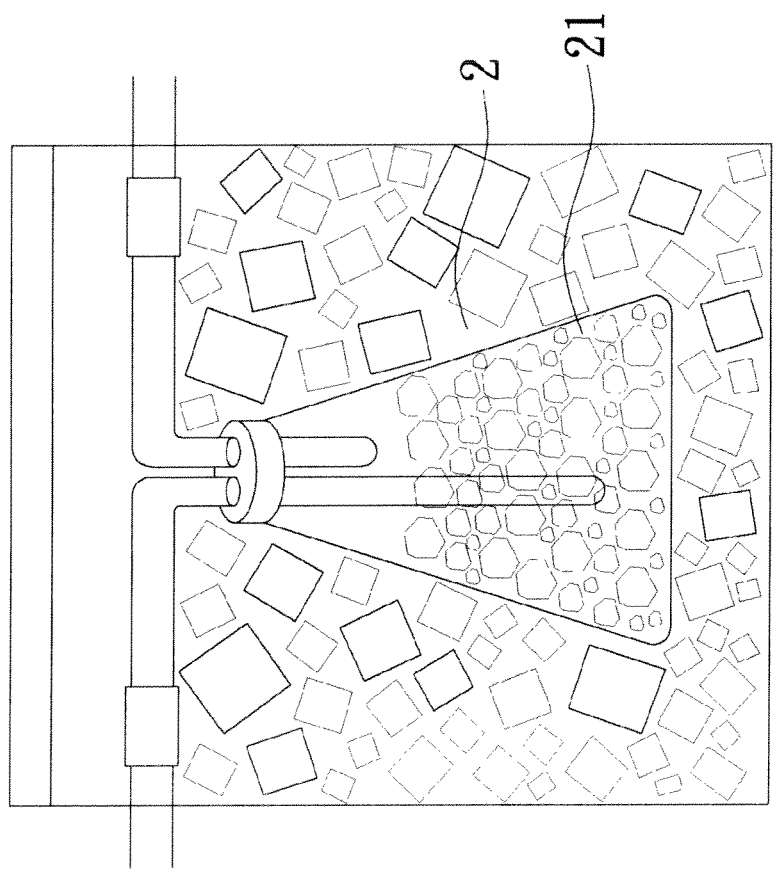
FIG. 4 shows a schematic view of a receiving container used in the method for making the slow releasing device according to the present invention.

With reference to FIG. 3, the low-temperature environment can be an interior of a refrigerator 3A. Various types of refrigerators providing an interior for receiving the receiving container 2 can be used. The refrigerator 3A can include an electronic temperature-controlling device 31 to control the temperature.

Figure 5A:
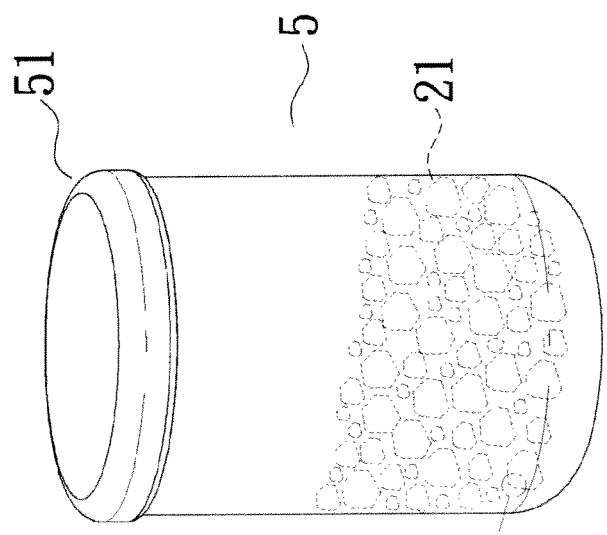
FIG. 5A shows a slow releasing device made by the method according to the present invention.
Figure 5C:
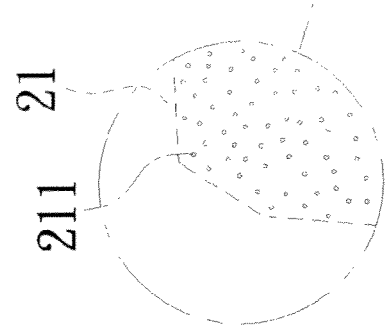
FIG. 5C shows an enlarged view of a circled portion of FIG. 5A.

With reference to FIG. 5A, the slow releasing device (the product) includes a sealed container 5 receiving a plurality of particulate carries 21. Each particulate carrier 21 has a plurality of pores 211 in a surface thereof. Gaseous chlorine dioxide is absorbed in the particulate carriers 21 in the sealed container 5. Preferably, each particulate carrier 21 is selected from a group consisting of celite, kaolinite, bentonite, zeolite, porphyries andesite, powders of bamboo charcoal, calcium oxide, calcium silicate, silica gel, porous ceramic balls, activated aluminum oxide, a molecular sieve, and combinations thereof. Preferably, the molecular sieve is one of crystalline alumino silicate and a carbon molecular sieve.

The low-temperature environment assists in absorption of gaseous chloride dioxide by the particulate carriers 21. The container 5 is preferably impermeable to air and light. The slow releasing device can be readily used by the user to release or use the gaseous chlorine dioxide. The disadvantages in conventional devices including instability, easy decomposition, and difficulties in carriage and transportation are solved. Thus, the product of gaseous chlorine dioxide according to the present invention is light and easy to carry and can be stored for a long period of time while allowing ready use of gaseous chlorine dioxide, achieving simplified use and easy accessibility.

Although specific embodiments have been illustrated and described, numerous modifications and variations are still possible without departing from the essence of the invention. The scope of the invention is limited by the accompanying claims.

The invention claimed is:

1. A method for making a slow releasing device for slowing releasing chlorine dioxide comprising:
    sending gaseous chlorine dioxide into a receiving container containing a plurality of particulate carriers, with each of the plurality of particulate carriers having a plurality of pores in a surface thereof, with the receiving container placed in a low-temperature environment below 30° C., with the gaseous chlorine dioxide absorbed by the plurality of particulate carriers;
    packaging the plurality of particulate carries in at least one container; and
    sealing said at least one container;
    wherein sending said gaseous chlorine dioxide into the receiving container further including sending gaseous chlorine dioxide from a gaseous chlorine dioxide generating source through an inlet pipe and passing through the gaseous chlorine dioxide through a purifying unit to purify the gaseous chlorine dioxide before entering the receiving container, with an outlet pipe connected to the receiving container, with superfluous gaseous chlorine dioxide not absorbed by the plurality of particulate carriers exiting the receiving container via the outlet pipe, with a circulating pipeline including a venturi connected to the outlet pipe, with a circulating pump mounted on the circulating pipeline and creating a suction force at the venturi, with an absorbing tank mounted on the circulating pipeline, with the absorbing tank capable of receiving water for dissolving or absorbing the superfluous gaseous chlorine dioxide.

2. The method as claimed in claim 1, wherein each of the plurality of particulate carriers is selected from a group consisting of celite, kaolinite, bentonite, zeolite, porphyries andesite, powders of bamboo charcoal, calcium oxide, calcium silicate, silica gel, porous ceramic balls, activated aluminum oxide, a molecular sieve, and combinations thereof.

3. The method as claimed in claim 2, wherein the molecular sieve is one of crystalline alumino silicate and a carbon molecular sieve.

4. The method as claimed in claim 1, wherein the low-temperature environment includes a trough receiving a cooling medium.

5. The method as claimed in claim 4, wherein the cooling medium is selected from a group consisting of low-temperature water, ice, dry ice, and liquefied nitrogen.

6. The method as claimed in claim 1, wherein the low-temperature environment is an interior of a refrigerator.

7. The method as claimed in claim 6, wherein the refrigerator includes an electronic temperature-controlling device.

* * * * *